(12) United States Patent
Tanaka et al.

(10) Patent No.: US 8,101,210 B2
(45) Date of Patent: Jan. 24, 2012

(54) USE OF CARBON DIOXIDE SUPPLYING MEANS FOR MUSCLE STRENGTHENING AND METHOD OF INCREASING CATTLE MEAT THEREBY

(75) Inventors: Masaya Tanaka, Kobe (JP); Masahiko Miwa, Kobe (JP)

(73) Assignees: Neochemir Inc., Kobe (JP); National University Corporation Kobe University, Kobe (JP)

( * ) Notice: Subject to any disclaimer, the term of this patent is extended or adjusted under 35 U.S.C. 154(b) by 53 days.

(21) Appl. No.: 12/739,718

(22) PCT Filed: Oct. 24, 2008

(86) PCT No.: PCT/JP2008/069351
§ 371 (c)(1),
(2), (4) Date: Apr. 23, 2010

(87) PCT Pub. No.: WO2009/054501
PCT Pub. Date: Apr. 30, 2009

(65) Prior Publication Data
US 2010/0247678 A1 Sep. 30, 2010

(30) Foreign Application Priority Data
Oct. 25, 2007 (JP) .................................. 2007-277524

(51) Int. Cl.
*A01N 59/04* (2006.01)
*A61K 33/00* (2006.01)
(52) U.S. Cl. ...................................................... 424/700
(58) Field of Classification Search .................. 424/700
See application file for complete search history.

(56) References Cited

U.S. PATENT DOCUMENTS

| 2002/0040205 A1 | 4/2002 | Rasor et al. |
| 2004/0219230 A1 | 11/2004 | Tanaka |
| 2005/0254993 A1* | 11/2005 | Tanaka ............................ 422/33 |
| 2006/0115560 A1* | 6/2006 | Long et al. ..................... 426/235 |

FOREIGN PATENT DOCUMENTS

| EP | 1 849 472 A1 | 10/2007 |
| JP | 2000-319187 A | 11/2000 |
| WO | WO 02/080941 A1 | 10/2002 |
| WO | WO 2004/002393 A1 | 1/2004 |
| WO | WO 2004/002393 A1 | 8/2004 |
| WO | WO 2006/080398 A1 | 8/2006 |
| WO | WO 2008/047829 A1 | 4/2008 |

OTHER PUBLICATIONS

Abstract only for JP-2004-511263-T Apr. 15, 2004.
S. Jonhagen et al., "Sports Massage After Eccentric Exercise", American Journal of Sports Medicine, 2004, vol. 32, No. 6, pp. 1499-1503.
Shoji Takaoka et al., "Kaku Massage Shugi ga Kinryoku Jikyuryoku ni Ataeru Eikyo", Journal of Oriental Medicine College Association, 2003, No. 27, pp. 50-53 with English language Machine Translation.

* cited by examiner

*Primary Examiner* — Johann Richter
*Assistant Examiner* — Thor Nielsen
(74) *Attorney, Agent, or Firm* — Birch, Stewart, Kolasch & Birch, LLP

(57) ABSTRACT

Use of a carbon dioxide-supplying means for muscle strengthening makes it possible conveniently to strengthen a target muscle within a short period of time merely by allowing the target site to absorb carbon dioxide without loading any mechanical burden on the target muscle. By loading a mechanical burden on the target muscle, the muscle strengthening effect can be further enhanced and an additional effect of promoting the recovery from muscle fatigue can be achieved owing to the mechanical burden. By using the carbon dioxide-supplying means for muscle strengthening as described above, it is also possible to increase cattle meat.

6 Claims, 5 Drawing Sheets

USE OF CARBON DIOXIDE SUPPLYING MEANS FOR MUSCLE STRENGTHENING AND METHOD OF INCREASING CATTLE MEAT THEREBY

TECHNICAL FIELD

The present invention relates to use of a carbon dioxide supplying means for muscle strengthening. More particularly, it relates to a muscle strengthening agent and a muscle strength decrease inhibitor containing carbon dioxide as an active ingredient, a muscle training method using the carbon dioxide supplying means, and a method of increasing cattle meat by using the carbon dioxide supplying means.

BACKGROUND ART

Patent Document 1 discloses that carbon dioxide is generally effective for the following symptoms (1) to (10) (see Patent Document 1):
(1) itching accompanying mucocutaneous diseases or mucocutaneous disorders such as athlete's foot, insect bite, atopic dermatitis, nummular eczema, xeroderma, seborrheic eczema, urticaria, prurigo, housewives' eczema, acne vulgaris, impetigo, folliculitis, carbuncle, furunculosis, phlegmon, pyoderma, psoriasis, ichthyosis, palmoplantar keratoderma, lichen, pityriasis, wound, burn, rhagades, erosion, and chilblain; mucocutaneous injuries such as decubitus ulcer, wound, burn, angular stomatitis, stomatitis, skin ulcer, rhagades, erosion, chilblain, and gangrene;
(2) incomplete engraftment of skin grafts, skin flaps etc.;
(3) dental diseases such as gingivitis, alveolar pyorrhea, denture ulcers, nigricans gingiva, and stomatitis;
(4) skin ulcers, cryesthesia and numbness caused by peripheral circulatory disorders such as thromboangitis obliterans, arteriolosclerosis obliterans, diabetic peripheral circulatory disorders, and lower limb varicosis;
(5) musculoskeletal diseases such as chronic rheumatoid arthritis, cervico-omo-brachial syndrome, myalgia, arthralgia and lumbago;
(6) nervous system diseases such as neuralgia, polyneuritis, and subacute myelo-optic neuropathy;
(7) keratoses such as psoriasis, corns, calluses, ichthyosis, palmoplantar keratoderma, lichen, and pityriasis;
(8) suppurative skin diseases such as acne vulgaris, impetigo, folliculitis, carbuncles, furuncles, phlegmon, pyoderma, and suppurative eczema;
(9) suppression of hair regrowth after depilation (treatment of unwanted hair); and
(10) cosmetic troubles with the skin or hair such as freckles, rough skin, loss of clarity of the skin, loss of elasticity or luster of the skin, and loss of glossiness of the hair, and partial obesity.

In order to achieve an improvement of the above-mentioned symptoms, as a carbon dioxide supplying means, a composition for preparing a carbon dioxide agent for external use (see Patent Documents 2 to 3), a carbon dioxide composition for external use (see Patent Document 4), a composition for preparing a carbon dioxide gel for external use (see Patent Document 5), a material for preparing a carbon dioxide agent for external use (see Patent Document 6), and a carbon dioxide external administration device (see Patent Documents 7 to 8) are disclosed.

Furthermore, Patent Document 9 discloses reduction of pain involved in musculoskeletal disorders by transdermal introduction of carbon dioxide.

However, use of a carbon dioxide supplying means for muscle strengthening, and more particularly, a muscle strengthening agent and a muscle strength decrease inhibitor containing carbon dioxide as an active ingredient, a muscle training method and a method of increasing cattle meat which use the carbon dioxide supplying means have not been known at all.

As a muscle strengthening method, muscle training in which a target muscle is contracted by the strength of 60% or more of the maximum muscle strength is common. In addition, kaatsu (pressure) muscle training is proposed, which is said to be capable of enhancing muscle strength within a shorter period of time by pressurizing a target muscle so as to inhibit the blood flow during the exercise.

The muscle strengthening method by the above-mentioned muscle training uses a phenomenon when muscle fatigue of a certain level or more is generated, the muscle strength is increased after a certain period of time has passed. In this case, recovery from fatigue is necessary because if the recovery from muscle fatigue is slow, fatigue accumulates, thus not only reducing the effect of the muscle training but also tending to cause injury and the like. Therefore, in order to increase the efficiency of muscle strengthening, the recovery from fatigue is carried out by means of massage, low frequency therapy apparatus, warm bath, and the like, after the muscle training. However, it is reported that massage does not have an effect of promoting muscle strengthening (see Non-patent Document 1). Therefore, massage is not thought useful for the recovery from fatigue.

As a method of increasing the amount of the muscle which does not need muscle training, a method of increasing the amount of the muscle by externally applying a heat load to a living body has been proposed (see Patent Document 10). In the present invention, "muscle strengthening" and "increasing the amount of the muscle" are intended to have the same meaning.

However, the method of increasing the amount of the muscle by applying a heat load described in Patent Document 10 requires accurate temperature management because the effective temperature for obtaining the effect of increasing the amount of the muscle (38 to 41° C.) approximates to the temperature at which tissue cells are killed (43° C.). When a living body is warmed by the use of an external heat source, the temperature of the skin is the highest and the temperature becomes lower toward the inside of the living body. Therefore, it is not easy to heat only the muscle at the effective temperature for a certain period of time or more.

Furthermore, the increasing of the amount of the muscle by this method needs such a long period of time as 14 weeks in order to increase, for example, the biceps brachii by 4% even when muscle training is carried out concurrently. Thus, this method is extremely ineffective.

Patent Document 1: Patent Document: Japanese Patent Unexamined Publication No. 2000-319187
Patent Document 2: Patent Document: National Publication of International Patent Application No. 2002/80941
Patent Document 3: Patent Document: National Publication of International Patent Application No. 2006/80398
Patent Document 4: Patent Document: National Publication of International Patent Application No. 2003/57228
Patent Document 5: Patent Document: National Publication of International Patent Application No. 2005/16290
Patent Document 6: Patent Document: National Publication of International Patent Application No. 2004/4745
Patent Document 7: Patent Document: National Publication of International Patent Application No. 2004/2393

Patent Document 8: Patent Document: National Publication of International Patent Application No. 2008/047829

Patent Document 9: Patent Document: U.S. Pat. No. 6,652,479B2

Patent Document 10: Patent Document: Japanese Patent Unexamined Publication No. 2006-61687

Non-patent Document 1: Non-patent Document 1: Sven Joenhagen et al., Sports Massage After Eccentric Exercise. The American Journal of Sports Medicine. 2004; 6: 1499-1503

DISCLOSURE OF THE INVENTION

Problems to be Solved by the Invention

The present invention has an object to provide use of a carbon dioxide supplying means for muscle strengthening, which makes it possible to obtain an effect within a short period of time in an easy and simple manner. Specifically, the present invention has an object to provide a muscle strengthening agent and a muscle strength decrease inhibitor containing carbon dioxide as an active ingredient, as well as a muscle training method and a method of increasing cattle meat which use the carbon dioxide supplying means. The present invention has a further object to concurrently provide an effect of promoting muscle strengthening and an effect of promoting recovery from fatigue in muscle training, and the like.

Means for Solving the Problems

The present inventors have found that by allowing a living body on a target site to absorb carbon dioxide with the use of a carbon dioxide supplying means for muscle strengthening, the muscle strength is enhanced or muscle strength decrease is suppressed. The inventors have also found that a carbon dioxide supplying means containing carbon dioxide as an active ingredient is useful as a muscle strengthening agent and a muscle strength decrease inhibitor. In addition, the inventors have found a muscle training method and a method of increasing cattle meat which use the carbon dioxide supplying means. Thus, the inventors have completed the present invention.

That is to say, the present invention provides use of a carbon dioxide supplying means for muscle strengthening.

According to the present invention, it is possible to promote muscle strengthening and recovery from fatigue in a target site concurrently.

In the present invention, the muscle strengthening agent containing carbon dioxide as an active ingredient includes any carbon dioxide-containing agents for external use for muscle strengthening. Examples of the muscle strengthening agent include gaseous carbon dioxide, carbon dioxide contained in a viscous composition, carbon dioxide dissolved in water of water vapor, carbon dioxide dissolved in a solvent capable of dissolving carbon dioxide, and the like. Administration techniques thereof may include nebulization, application, patch, and the like. The administration techniques are not particularly limited as long as they are methods by which carbon dioxide can be supplied to a target site. Furthermore, the muscle strength decrease inhibitor containing carbon dioxide as an active ingredient includes any carbon dioxide-containing agents for external use for suppressing the decrease in muscle strength. Examples of the muscle strength decrease inhibitor include gaseous carbon dioxide, carbon dioxide contained in a viscous composition, carbon dioxide dissolved in water of water vapor, carbon dioxide dissolved in a solvent capable of dissolving carbon dioxide, and the like. Administration techniques thereof may include nebulization, application, patch, and the like. The administration techniques are not particularly limited as long as they are methods by which carbon dioxide can be supplied to a target site.

The present invention is a muscle strengthening agent and a muscle strength decrease inhibitor containing carbon dioxide as an active ingredient.

The present invention is the muscle strengthening agent and the muscle strength decrease inhibitor by which carbon dioxide is locally administered by using one or more carbon dioxide supplying means selected from the group consisting of a carbon dioxide external administration device, a carbon dioxide agent for external use, a carbonated spring, water vapor containing carbon dioxide, and an intra-tissue injection of carbon dioxide.

The present invention is the muscle strengthening agent and the muscle strength decrease inhibitor by which carbon dioxide is transdermally administered by using the carbon dioxide external administration device.

The present invention is the muscle strengthening agent and the muscle strength decrease inhibitor using the above mentioned carbon dioxide external administration device, which is characterized by including a sealing enclosure member capable of sealing a body surface from the outside air, a supplying device for supplying carbon dioxide into the inside of the sealing enclosure member, and an absorption aid for assisting transdermal or transmucosal absorption of the carbon dioxide inside the sealing enclosure member.

The present invention is a muscle training method including a combination of transdermal absorption of carbon dioxide using one or more carbon dioxide supplying means selected from the group consisting of a carbon dioxide external administration device, a carbon dioxide agent for external use, a carbonated spring, water vapor containing carbon dioxide, and an intra-tissue injection of carbon dioxide, and applying a load to a target muscle and/or inhibiting the blood flow to the muscle.

The present invention provides a muscle training method including a combination of a transdermal absorption of carbon dioxide using a carbon dioxide external administration device characterized by including a sealing enclosure member capable of sealing a body surface from the outside air, a supplying device for supplying carbon dioxide into the inside of the sealing enclosure member, and an absorption aid for assisting transdermal or transmucosal absorption of the carbon dioxide inside the sealing enclosure member; and applying a load to a target muscle and/or inhibiting the blood flow to the muscle.

The present invention is a muscle training method including a combination of a transdermal absorption of carbon dioxide using a carbon dioxide external administration device characterized by including a sealing enclosure member capable of sealing a body surface of a human or an animal from the outside air, a supplying device for supplying carbon dioxide into the inside of the sealing enclosure member, and a perspiration promoting means for promoting perspiration on the body surface inside the sealing enclosure member; and applying a load to a target muscle and/or inhibiting the blood flow to the muscle.

The present invention is a method of increasing cattle meat characterized by using one or more carbon dioxide supplying means selected from the group consisting of a carbon dioxide external administration device, a carbon dioxide agent for external use, a carbonated spring, water vapor containing carbon dioxide, and an intra-tissue injection of carbon dioxide.

Advantages of the Invention

A muscle strengthening agent and a muscle strength decrease inhibitor of the present invention make it possible to enhance the muscle strength or suppress muscle strength decrease within a short period of time in an easy and simple manner when they are applied to aged persons whose muscle strength is weakened or patients who have pain in the lower back, the elbow or the knee, who have difficulty in performing muscle training. The enhancement of the muscle strength or suppression of muscle strength decrease increases the physical ability for behavior, and therefore enables independence of behavior to be improved, the area of movement to be enlarged, and the quality of life to be improved in aged persons or patients whose muscle strength is weakened. Since the muscle strengthening agent and the muscle strength decrease inhibitor of the present invention can be easily applied to bedridden patients, and the like, they can promote recovery in such patients and prevent disorders such as disuse atrophy. The muscle strengthening agent and the muscle strength decrease inhibitor of the present invention can prevent muscle strength decrease and arthrogryposis occurring at the time when a fraction site or the like is fixed by applying a plastic cast with a function of a sealing enclosure member described in Patent Document 7 (Japanese Patent Unexamined Publication No. 2004-517345). When the muscle strengthening agent and/or the muscle strength decrease inhibitor of the present invention is applied during rehabilitation after fixing is completed, recovery of the muscle strength is promoted and the number of dates required for rehabilitation can be shortened. In addition, the muscle strengthening agent and the muscle strength decrease inhibitor of the present invention are effective when the muscle strength is decreased at the time of numbness by cerebrovascular disorder, spinal cord damage, bed rest after surgical operation, and the like.

As the muscle strengthening agent and the muscle strength decrease inhibitor of the present invention, a portable carbon dioxide transdermal absorption means such as a composition for preparing a carbon dioxide agent for external use and a carbon dioxide external administration device can be used. Therefore, it is possible to enhance the muscle strength and/or to suppress muscle strength decrease easily even if specific facilities such as a gymnasium and a rehabilitation room are not available.

The muscle strengthening agent and the muscle strength decrease inhibitor of the present invention are not affected by the gravity. Therefore, when, for example, astronauts use the muscle strengthening agent and the muscle strength decrease inhibitor during a rest or sleeping time, the time required to do exercise for preventing deterioration of physical functions can be shortened. Thus, they can spend more time in their tasks such as scientific experiments efficiently.

The muscle strengthening agent and the muscle strength decrease inhibitor of the present invention not only promote muscle strengthening in a short period of time by muscle training but also promote recovery from fatigue in athletes, thus enabling their physical abilities to be improved efficiently and safely.

Needless to say, since the muscle strengthening agent and the muscle strength decrease inhibitor of the present invention can be applied to animals, for example, running ability of racehorses can be improved efficiently and safely. Furthermore, use of the carbon dioxide supplying means for muscle strengthening of the present invention can also increase meat of cattle such as cow, pig, and sheep safely and efficiently.

BEST MODE FOR CARRYING OUT THE INVENTION

Figure 1:
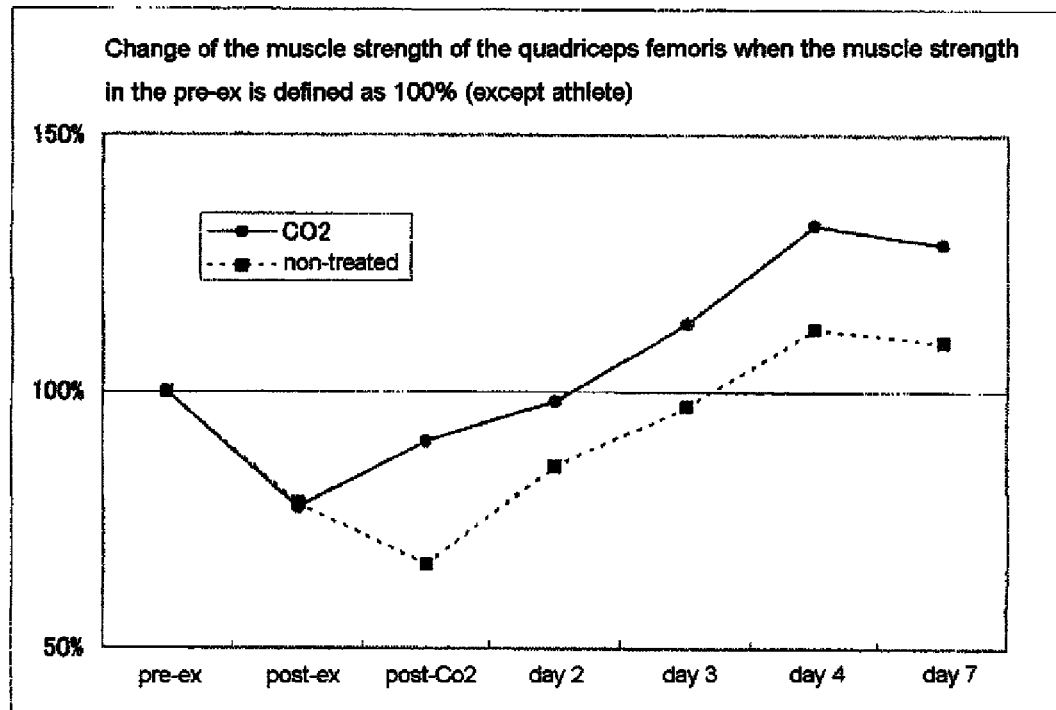
FIG. 1 is a graph showing the change of the muscle strength of the quadriceps femoris when the muscle strength in the pre-ex (before an exercise load is given. The "ex" denotes a stretching exercise on isometric torque of the quadriceps femoris. The same is true hereinafter.) is defined as 100%.

Use of a carbon dioxide supplying means for muscle strengthening in accordance with the present invention is not particularly limited as long as it allows a living body to absorb carbon dioxide. However, a local absorption means is preferred. An example of the carbon dioxide supplying means for allowing a living body to absorb carbon dioxide may include the followings.

(1) A composition for preparing carbon dioxide agents for external use, for example, carbon dioxide agents for external use obtained from the following a) and b): a) a composition for preparing a carbon dioxide agent for external use characterized by comprising a substance generating an acid after being hydrolyzed, a carbonate, a thickener, and water as essential components, and further comprising a gelating agent being gelated by calcium ion, and a water-insoluble or poorly-soluble calcium salt (National Publication of International Patent Application No. 2006/80398), or b) a composition for preparing a carbon dioxide agent for external use comprising a granular material containing a water-soluble acid, a thickener, and a water-soluble dispersant as the essential components in which the thickener is mixed with the water-soluble acid and the water-soluble acid and the water-soluble dispersant; and a viscous composition containing a carbonate, water, and a thickener as the essential components, which is to be mixed with the granular material at use (National Publication of International Patent Application No. 2002-80941).

(2) A carbon dioxide composition for external use, characterized in that carbon dioxide is dissolved in a non-bubble state in a viscous material comprising at least water and a thickener, or a carbon dioxide composition for external use characterized by comprising at least a fermentation microbe, a metabolite of the fermentation microbe, a thickener, water, and carbon dioxide (National Publication of International Patent Application No. 2003/57228).

(3) A carbon dioxide agents for external use obtained from a composition for preparing a carbon dioxide gel for external use characterized by comprising the following granular material (A) and viscous material (B) to be mixed with the granular material (A):

(A) a granular material comprising a weak acid and a calcium ion trapping agent as essential components; and (B) a viscous material comprising calcium carbonate, a gelling agent gelled by calcium ions and water as essential components (see, National Publication of International Patent Application No. 2005/16290).

(4) A carbon dioxide external administration device, characterized by comprising a sealing enclosure member capable of sealing a body surface from the outside air, a supply means for supplying carbon dioxide into the inside of the sealing enclosure member, and an absorption aid that assists transdermal or transmucosal absorption of the carbon dioxide inside the sealing enclosure member (National Publication of International Patent Application No. 2004/02393).

(5) A carbon dioxide external administration device, characterized by comprising a sealing enclosure member capable of sealing a body surface of a human or an animal from the outside air, a supply means for supplying carbon dioxide into the inside of the sealing enclosure member, and a perspiration promoting means for promoting perspiration on the body surface inside the sealing enclosure member (National Publication of International Patent Application No. 2008/047829).

In addition, a carbonated spring such as an artificial carbonated spring and water vapor containing carbon dioxide can also be used. The water vapor containing carbon dioxide denotes, for example, natural vapor that contains carbon dioxide and is erupted from underground, and water vapor white smoke that contains carbon dioxide, which is generated when dry ice is put in the air. The water vapor containing carbon dioxide is used for hemorrhoid treatment, and the like, in for example, East Europe. Furthermore, a method of injecting carbon dioxide directly into target tissue with the use of a syringe, and the like, can be employed. Needless to say, the present invention is not limited to these carbon dioxide supplying means, and may include any means that allow a target site to absorb carbon dioxide in an amount capable of promoting muscle strengthening. Among them, the carbon dioxide external administration devices described in the above-mentioned (4) or (5) are preferred.

The above-mentioned carbon dioxide supplying means may also be applied to muscle training. When the use of the carbon dioxide supplying means for muscle strengthening of the present invention is employed in muscle training, the absorption of carbon dioxide may be carried out at any time from before, during or after the muscle training. However, the absorption of carbon dioxide is preferably after the muscle training because an effect of recovery from fatigue is strong. In the present invention, the muscle training includes so-called kaatsu training, that is, training while the muscle is pressurized by various methods.

As a concentration of carbon dioxide to be absorbed and absorption time may vary depending upon carbon dioxide supplying means to be used. In the case where a carbon dioxide external administration device is used, the carbon dioxide concentration is preferably 300 ppm or more, and more preferably 1,000 ppm or more. The absorption time may be preferably about five minutes or more, and more preferably ten minutes or more. Since carbon dioxide has highly safety, its absorption for a long period of time does not matter. However, an expected effect can be obtained in about 30 minutes.

When a carbon dioxide agent for external use, for example, the composition for external use mentioned above (2) is used, the concentration of carbon dioxide to be dissolved is preferably 300 ppm or more, and particularly preferably in the range from 1,000 ppm to the saturation concentration.

Absorption frequency of carbon dioxide is preferably once or more a week, and more preferably once or more a day.

When use of the carbon dioxide supplying means for muscle strengthening of the present invention is carried out concurrently with muscle training, it is preferable that absorption of carbon dioxide is carried out every time muscle training is carried out. However, expected effect can substantially be obtained even when the absorption of carbon dioxide is skipped once in several times. It is preferable that the absorption of carbon dioxide is carried out even in days when muscle training is not carried out because muscle strengthening and recovery from fatigue are promoted.

EXAMPLES

Hereinafter, the present invention will be specifically described with reference to Examples. However, the present invention is not limited to these Examples.

Example 1

Promotion of Muscle Strengthening by Stretching Exercise on Isometric Torque of Legs (a carbon dioxide external administration device was used as a carbon dioxide supplying means for muscle strengthening)

[Experiment Method]

Eight subjects including two subjects who played sports three times or more a week (hereinafter, referred to as "athlete") and six subjects who played sports two times or less a week (hereinafter, referred to as "non-athlete") participated in the experiment. Each subject did warming-up by pedaling a gym bicycle for ten minutes. Next, each subject did a stretching exercise on isometric torque of the quadriceps femoris 300 times or more by using training machine MyoretRZ-450 (Kawasaki Heavy Industries, Ltd.). Thus, an exercise load was applied to the quadriceps femoris. Then, the muscle strength of the quadriceps femoris and the muscle strength of the hamstrings to which an exercise load was not applied were measured by using MyoretRZ-450.

After the training was completed, the carbon dioxide absorption aid 4 described in Example 5 in Patent Document 7 (Japanese Patent Unexamined Publication No. 2004-517345) was applied to one determined leg (hereinafter, referred to as a "treated leg"). The treated leg was covered with an 80 cm-long polypropylene bag type sealing enclosure member equipped with a check valve. Then, the member was filled with carbon dioxide from a carbon dioxide gas cylinder and stood still for ten minutes. The carbon dioxide concentration was set to 80% (800,000 ppm). No treatment was given to the other leg (hereinafter, referred to as a "non-treated leg"). The training was carried out only once, this time.

For three days from the next day after the training, each subject did not do a stretching exercise on isometric torque of the quadriceps femoris. Each subject allowed the treated leg to absorb carbon dioxide for ten minutes once a day as mentioned above by using the carbon dioxide supplying means for muscle strengthening of the present invention (by using a carbon dioxide external administration device as the carbon dioxide supplying means). Thereafter, the muscle strength of the quadriceps femoris and the muscle strength of the hamstrings were measured by using MyoretRZ-450.

On day 4 and later after the experiment was started, neither absorption of carbon dioxide nor stretching exercise on isometric torque of the quadriceps femoris was carried out. On day 7 after the experiment was started, the muscle strengths of the quadriceps femoris and the hamstrings were measured by using MyoretRZ-450.
[Experiment Results]
On the day of starting the experiment, about 25% decrease of the muscle strength was observed in both legs after the exercise load was applied (see post-ex in FIG. 1) when the muscle strength before an exercise load was applied (pre-ex) was defined as 100%.

During the absorption of carbon dioxide after the exercise load was applied, blood pressure and heart rate of the subjects did not change. After carbon dioxide was absorbed, when the muscle strength of the quadriceps femoris was measured by using MyoretRZ-450, recovery of the muscle strength was faster in the treated leg than in the non-treated leg (see post-CO2 in FIG. 1).

On days 2 to 4 of the experiment, when the muscle strength of the quadriceps femoris was measured by using MyoretRZ-450, muscle strengthening was observed in both legs. The muscle strengthening was promoted in the treated leg as compared with in the non-treated leg (see on days 2, 3, and 4 in FIG. 1).

On day 7 of the experiment, when the muscle strength of the quadriceps femoris was measured, only slight muscle strengthening was observed in the non-treated leg. Meanwhile, in the treated leg, although the absorption of carbon dioxide had been stopped, 20% muscle strengthening was observed. In particular, in the non-athletes, about 30% muscle strengthening was observed (see the result on day 7 in FIG. 1).

Figure 2:
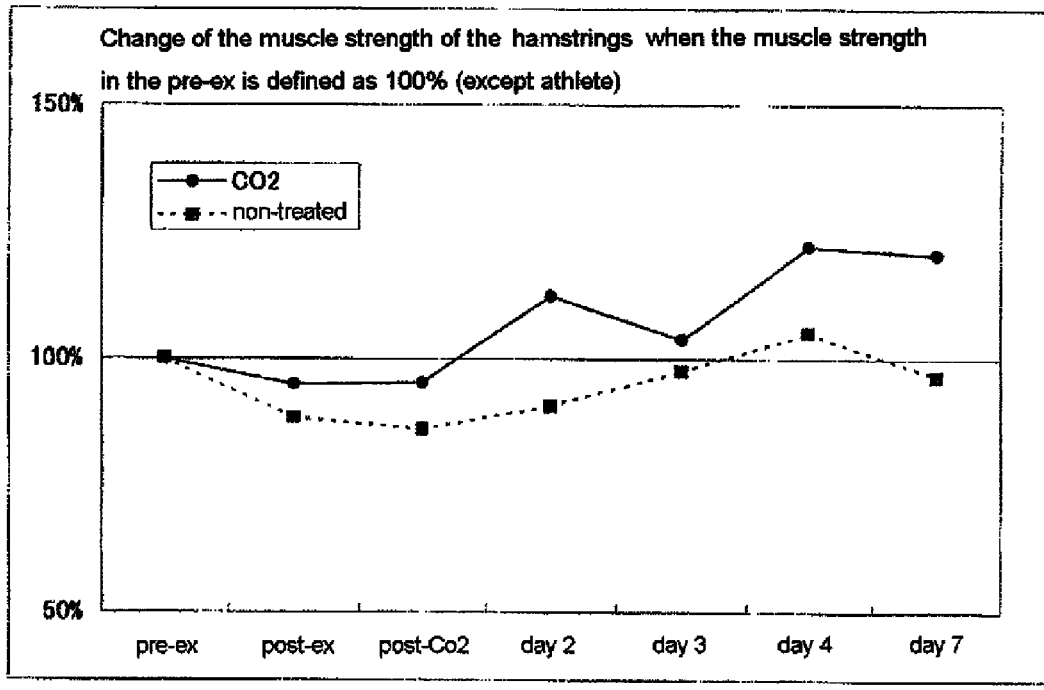
FIG. 2 is a graph showing the change of the muscle strength of the hamstrings when the muscle strength in the pre-ex is defined as 100%.
Figure 3:
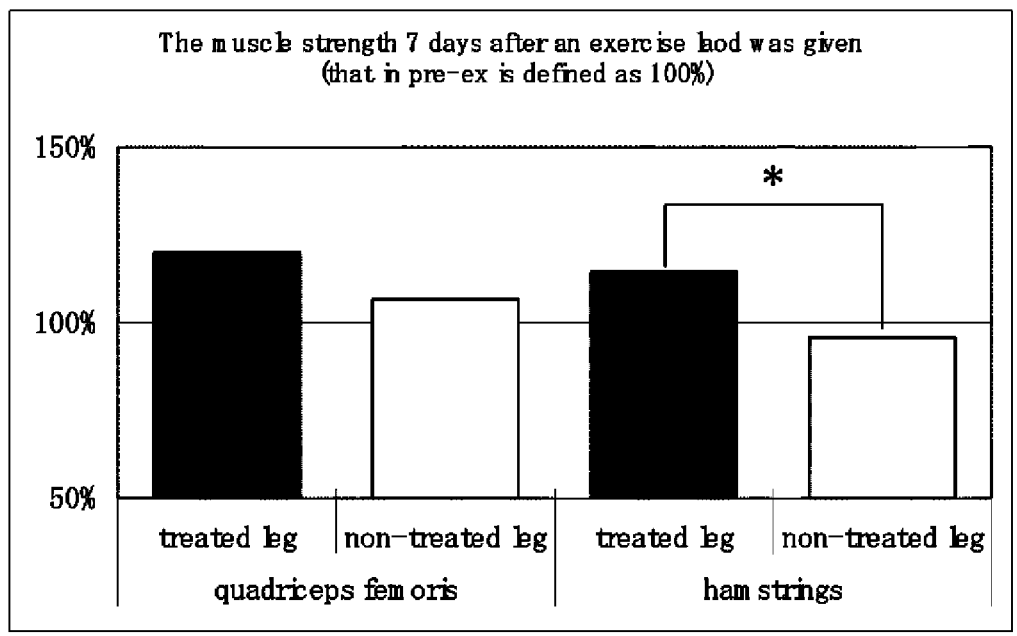
FIG. 3 is a graph showing the muscle strength of the quadriceps femoris and the muscle strength of the hamstrings seven days after an exercise load is given, when the muscle strength in the pre-ex is defined as 100%.

On the other hand, also in the hamstrings to which an exercise load was not given, about 15% muscle strengthening was observed in the treated leg while muscle strengthening of the hamstrings was not observed in the non-treated leg (see the result on day 7 in FIG. 2). As is apparent from FIG. 3, the muscle strengthening was statistically significant at $P=5\%$. Furthermore, as is apparent from FIG. 2, in particular, in the case of non-athletes, about 20% muscle strengthening was observed.

Example 2

Promotion of Muscle Strengthening with No Exercise Load Applied (a carbon dioxide external administration device was used as a carbon dioxide supplying means for muscle strengthening)
[Experiment Method]
Thirteen subjects (all males, aged from 27 to 43) participated in the experiment. In each subjects, the absorption aid 4 of carbon dioxide described in Example 5 in Patent Document 7 (Japanese Patent Unexamined Publication No. 2004-517345) was given to one determined leg (hereinafter, referred to as a "treated leg"). The treated leg was covered with an 80 cm-long polypropylene bag type sealing enclosure member equipped with a check valve. Then, carbon dioxide was filled in the member from a carbon dioxide gas cylinder and stood still for ten minutes. The carbon dioxide concentration was set to 80% (800,000 ppm). The treatment was carried out at least once a week for three months. No treatment was given to the other leg (hereinafter, referred to as a "non-treated leg"). Before and three months after the experiment was started, the muscle strengths of the treated leg and the non-treated leg were measured (the muscle strengths of the quadriceps femoris and the hamstrings were measured by using MyoretRZ-450).

Figure 4:
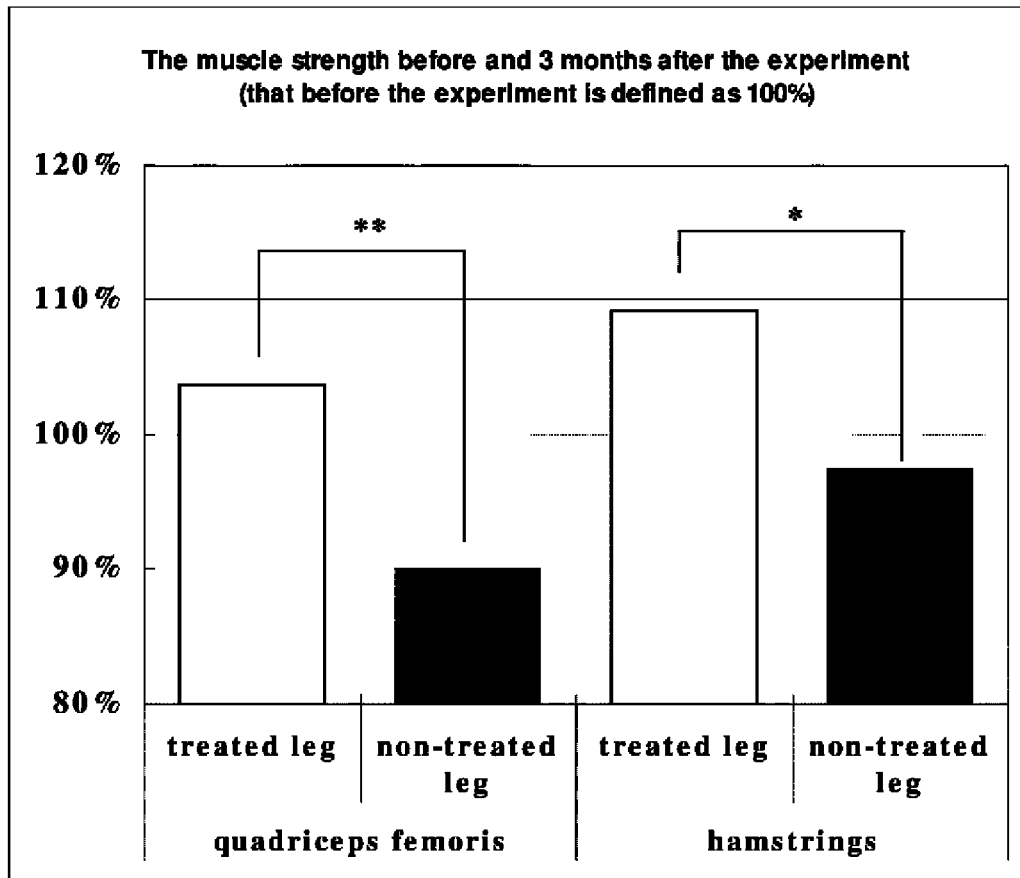
FIG. 4 is a graph showing the muscle strength after the three-months experiment in a case where an exercise load is not given.

[Experiment Results]
On month 3, about 15% muscle strengthening was observed in the quadriceps femoris and the hamstrings in the treated leg as compared with the non-treated leg. The muscle strengthening were statistically significant at $P=1\%$ in the quadriceps femoris and $P=5\%$ in the hamstrings (see FIG. 4).

Example 3

Increase in Amount of Rat Muscle with No Exercise Load Applied (a carbon dioxide external administration device was used as a carbon dioxide supplying means for muscle strengthening)
[Experiment Method]
Nine male Wister rats (5-week old at the time when the experiment was started) were used. The rats were divided into two groups: a group of rats that underwent absorption of carbon dioxide (hereinafter, referred to as a "CO2 group") and a group of rats that did not undergo absorption of carbon dioxide (hereinafter, referred to as a "CONTROL group").

In the CO2 group, the hair was removed from the right and left lower thighs of six rats under anesthesia. Then, the absorption aid 4 of carbon dioxide described in Example 5 in Patent Document 7 (Japanese Patent Unexamined Publication No. 2004-517345) was applied to only the right lower thigh (hereinafter, referred to as a "treated limb"). Next, the rat lower body was covered with a polyethylene bag type sealing enclosure member provided with a hole through which the left hind limb comes out so that only the right hind limb absorbs carbon dioxide. Then, carbon dioxide was filled in the sealing enclosure member by using a carbon dioxide gas cylinder so as to inflate the sealing enclosure member. In order to always secure a sufficient amount of carbon dioxide in the sealing enclosure member, carbon dioxide was added at any time, so that the sealing enclosure member was filled with carbon dioxide for ten minutes. The carbon dioxide concentration inside the sealing enclosure member was set to 100%. The above-mentioned treatment was carried out twice a week for three months. To the left lower thigh, only removing of hair was carried out and other treatment was not carried out (hereinafter, referred to as "non-treated leg").

In the CONTROL group, only anesthesia was carried out and absorption of carbon dioxide was not carried out.

Figure 5:
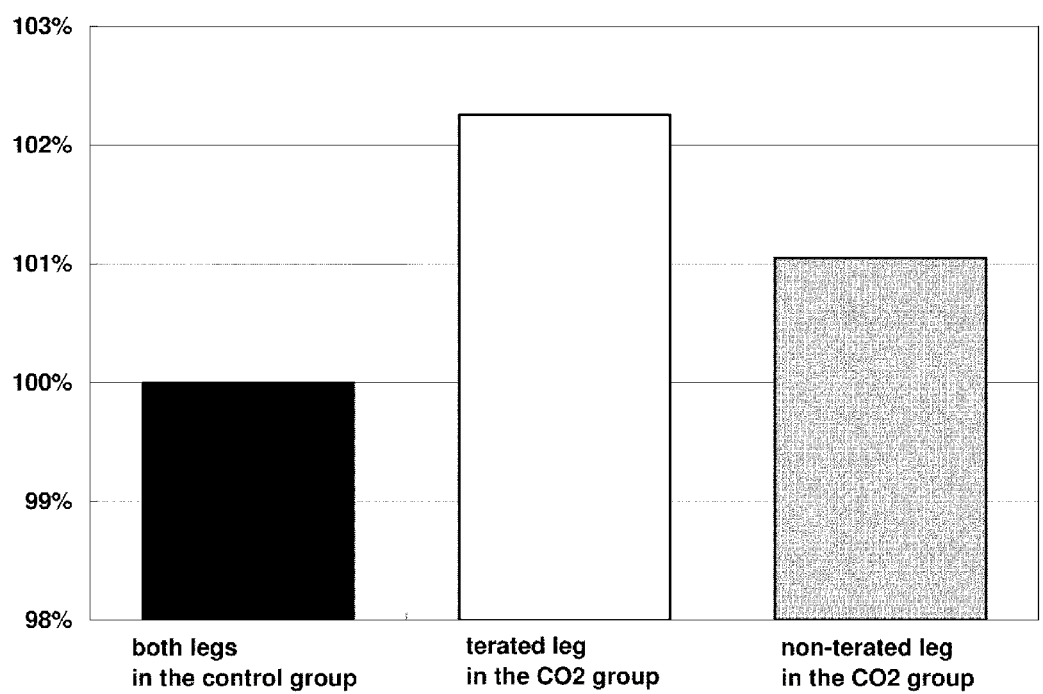
FIG. 5 is a graph showing the ratio of lower limb muscle wet weight to body weight of rat after the three-months experiment in a case where an exercise load is not given.
Figure 6:
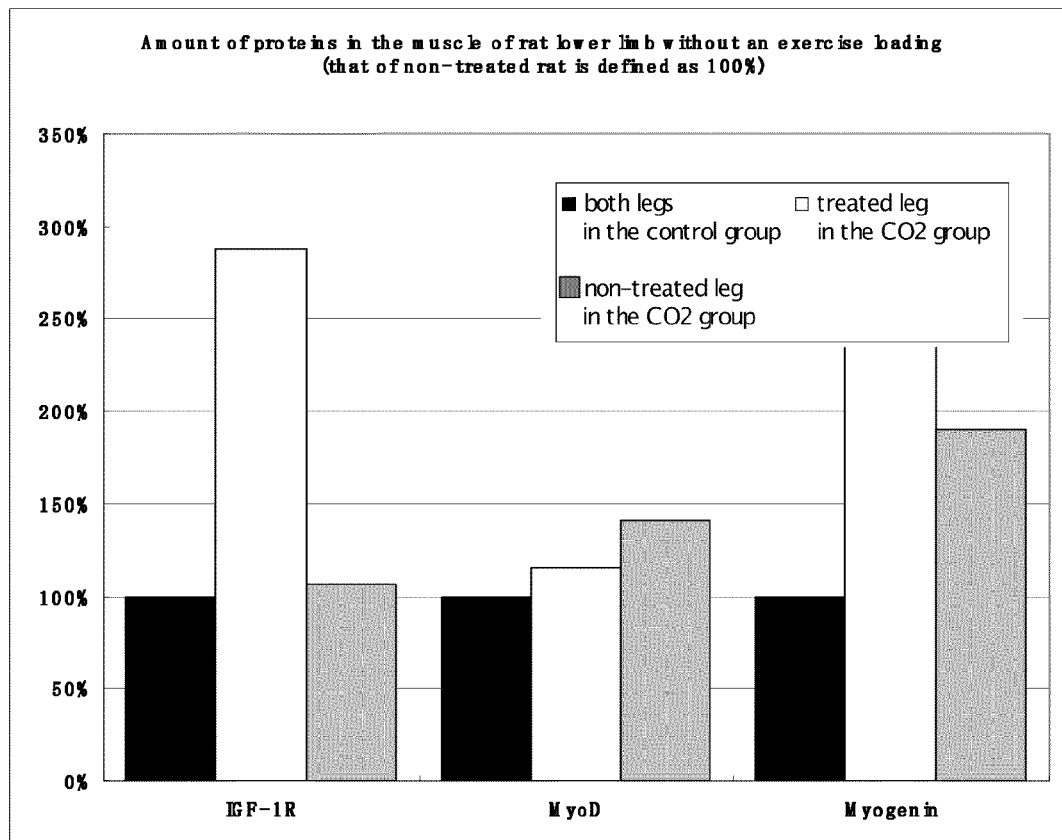
FIG. 6 is a graph showing amounts of proteins extracted from the muscle of rat lower limb of the three-months experiment in a case where an exercise load is not given.

Three months later, the rat body weights were measured and the muscle was collected from the right and left lower thighs. The muscle wet weight of the collected muscle was measured, followed by detecting growth a acceleration indicating proteins of muscle fibers, MyoD and Myogenin (see Atsuko HARA et al., "Expression of myosin heavy chain isoforms, myogenin and MyoD in the course of regeneration of skeletal muscle," Journal of Health Sciences of Hiroshima University, Vol. 2 (1): 12-18, 2002), and IGF-IR [see Junichi SUZUKI et al., "Effect of endurance training with L-arginine supplementation on expression of IGF-1 receptor in rat skeletal muscles" Research for Winter Sports, (the Proceedings of Research and Education Center for Winter Sports, Hokkaido University of Education), Vol. 8 (1) 1-7, 2005], by Western blotting. The resultant bands were analyzed on the analysis software (NIH-Image) so as to quantify each growth acceleration indicating protein. The resultant ratio of the muscle wet weight/body weight thus obtained is shown in FIG. 5 and the amount of each protein is shown in FIG. 6.
[Experiment Results]
As is apparent from FIG. 5, when the muscle wet weight and the body weight were measured, an increase in the muscle wet weight per body weight was observed in the CO2 group as compared with the CONTROL group. Furthermore, in the CO2 group, a remarkable increase in the muscle wet weight was observed in the treated leg as compared with the non-treated leg.

As is apparent from FIG. 6, the amount of the growth acceleration indicating protein extracted from the muscle of the CO2 group was increased as compared with that of the CONTROL group.

These experiment results show that the muscle wet weight is increased by the absorption of carbon dioxide, and the increase is brought about by the growth acceleration of the muscle fiber.

Example 4

Promotion of Kaatsu Training Effect (a carbon dioxide external administration device was used as a carbon dioxide supplying means for muscle strengthening)

[Experiment Method]

Two subjects (one male and one female) participated in the experiment. The experiment was carried out according to Abe T. et al. (2006) Electromyographic responses of arm and chest muscle during bench press exercise with and without KAATSU. Int. J. Kaatsu Training Res. 2:15-18. The grip strengths of both hands of each subject were measured before the experiment was started. Next, the absorption aid 4 of carbon dioxide described in Example 5 in Patent Document 7 (Japanese Patent Unexamined Publication No. 2004-517345) was applied to the entire left arm of each subject, and the left arm was covered with an 80 cm-long polypropylene bag type sealing enclosure member equipped with a check valve. A cuff of blood pressure manometer was worn on the upper arm with the sealing enclosure member applied. Firstly, the upper arm was pressurized with a cuff pressure of 50 mmHg for 30 seconds. Next, the pressure was released once for 10 seconds, and then the upper arm was pressurized while gradually increasing the cuff pressure to 70 mmHg. When the cuff pressure reached 70 mmHg, the pressure was fixed. Then, carbon dioxide was filled in the sealing enclosure member from a carbon dioxide gas cylinder so as to inflate the sealing enclosure member. Immediately thereafter, the subjects carried out an exercise of opening and closing the palm 20 times quickly, and then took a rest for 15 seconds. This exercise and rest were repeated three times (hereinafter, this arm is referred to as a "treated arm"). In order to always secure a sufficient amount of carbon dioxide in the sealing enclosure member, carbon dioxide was added at any time. Ten minutes after the initial pressurizing, the cuff pressure was released, and the sealing enclosure member was removed.

In the right arm, only pressurizing and exercise of opening and closing the palm were carried out under the same condition as in the left arm, and absorption of carbon dioxide was not carried out (hereinafter, this arm is referred to as a "non-treated arm").

Three days after the experiment, the grip strength of both hands of each subject was measured.

[Experiment Results]

Figure 7:
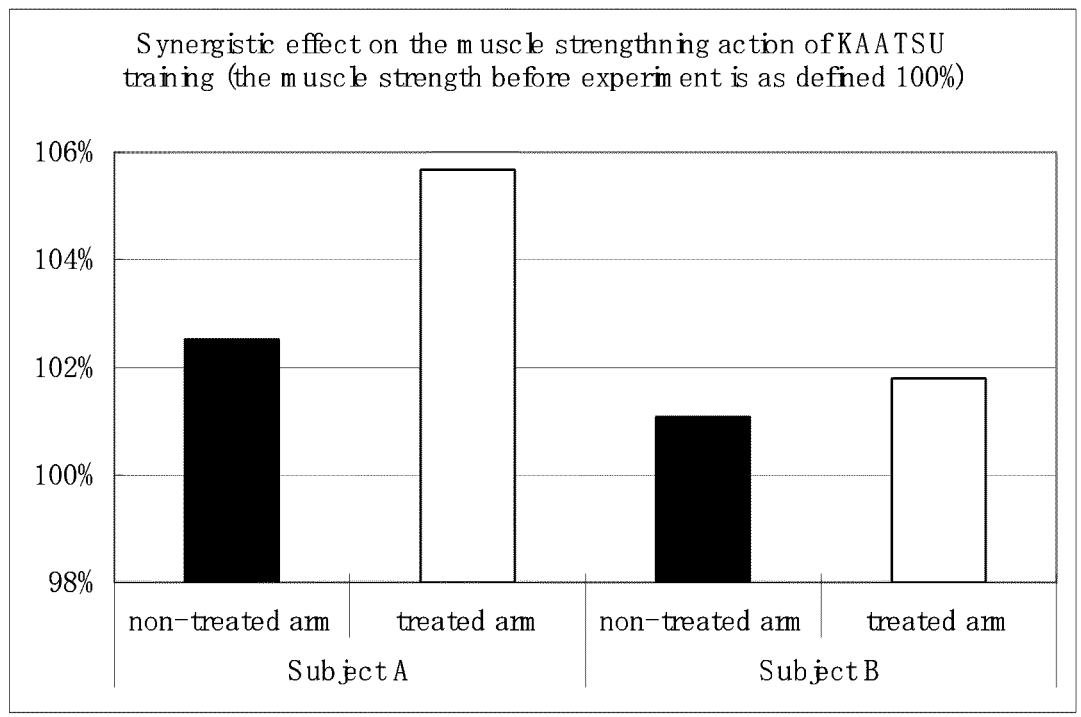
FIG. 7 is a graph showing the grip strength on day 3 after kaatsu training is carried out.

As is apparent from FIG. 7, it was shown that absorption of carbon dioxide promoted the muscle strengthening effect by pressurizing. As compared with the case in which only pressurizing was carried out by using a carbon dioxide supplying means for muscle strengthening, almost two-times muscle strengthening rate was shown. Training of only pressurizing and an exercise of opening and closing the palm accompanies a sever muscle pain or fatigue. However, in the left hand, which had undergone the same training while allowing carbon dioxide to be absorbed with the use of the carbon dioxide supplying means for muscle strengthening, the muscle pain and fatigue were reduced.

INDUSTRIAL APPLICABILITY

A muscle strengthening agent and a muscle strength decrease inhibitor of the present invention containing carbon dioxide as an active ingredient make it possible to enhance the muscle strength or to suppress muscle strength decrease in the muscle in a target site in an easy and simple manner within a short period of time merely by allowing a target muscle to absorb carbon dioxide without applying any mechanical loads to the target muscle. Furthermore, the muscle strengthening agent and the muscle strength decrease inhibitor of the present invention containing carbon dioxide as an active ingredient are useful as a muscle training method in promoting muscle strengthening or suppressing the muscle strength decrease in a combination of applying a load to a target muscle and/or inhibiting the blood flow. Use of the carbon dioxide supplying means for muscle strengthening of the present invention makes it possible to increase an amount of cattle meat.

The invention claimed is:

1. A method of increasing cattle meat characterized by transdermally administrating carbon dioxide at a target site by using one or more carbon dioxide supplying systems selected from the group consisting of a carbon dioxide external administration device, a carbon dioxide agent for external use, a carbonated spring, water vapor containing carbon dioxide, and an intra-tissue injection of carbon dioxide.

2. The method of increasing cattle meat according to claim 1, wherein the carbon dioxide supplying system is selected from the group of gaseous carbon dioxide and water vapor containing carbon dioxide.

3. The method of increasing cattle meat according to claim 1, wherein carbon dioxide is administrated with a carbon dioxide external administration device characterized by comprising a sealing enclosure member capable of sealing a body surface from the outside air, a supply means for supplying carbon dioxide into the inside of the sealing enclosure member, and an absorption aid comprised of a viscous material containing a thickener and water which assists transdermal or transmucosal absorption of the carbon dioxide inside the sealing enclosure member.

4. The method of increasing cattle meat according to claim 3, wherein the thickener is selected from sodium alginate and sodium carboxymethylcellulose.

5. The method of increasing cattle meat according to claim 1, wherein the carbon dioxide supplying systems is a carbon dioxide agent for external use.

6. The method of increasing cattle meat according to claim 5, wherein the concentration of carbon dioxide is equal to or over 300 ppm.

* * * * *